United States Patent [19]

Arauner

[11] 4,034,228

[45] July 5, 1977

[54] TUBUS FOR DETERMINING THE BOUNDARIES OF A BEAM OF PENETRATING RAYS

[75] Inventor: Alfred Arauner, Furth, Germany

[73] Assignee: Siemens Aktiengesellschaft, Berlin & Munich, Germany

[22] Filed: Sept. 29, 1975

[21] Appl. No.: 617,579

[30] Foreign Application Priority Data

Sept. 30, 1974 Germany ............... 2446680

[52] U.S. Cl. ........................... 250/511
[51] Int. Cl.² ............... G21F 5/04; G21K 1/04
[58] Field of Search .......... 250/511, 512, 513, 505

[56] References Cited

UNITED STATES PATENTS

| 1,909,118 | 5/1933 | Raab | 250/513 |
|---|---|---|---|
| 2,542,196 | 2/1951 | Haupt | 250/513 |
| 2,570,820 | 10/1951 | Knab | 250/511 |
| 3,942,019 | 3/1976 | Claridge et al. | 250/512 |

Primary Examiner—Alfred E. Smith
Assistant Examiner—T. N. Grigsby
Attorney, Agent, or Firm—Hill, Gross, Simpson, Van Santen, Steadman, Chiara & Simpson

[57] ABSTRACT

A tubus for defining the boundary of a beam of penetrating rays, which is preferably adapted for use in the radiation therapy. In a tubus of the above-mentioned type, the tube wall is thereby constructed of a plurality of over-lapping wall elements directed in parallel with the edge radiation of the radiation cone encompassed by the tubus, and suspended on the tubus housing so as to be displaceable to the direction of the edge radiation. That type of construction of the tubus facilitates the cross-section and also the surface of the focused radiation cone to be varied. Thereby it becomes possible to correlate the radiation field in a stepless manner by means of one and the same tubus over a wide range to almost every form and size of the illness spread.

7 Claims, 10 Drawing Figures

TUBUS FOR DETERMINING THE BOUNDARIES OF A BEAM OF PENETRATING RAYS

FIELD OF THE INVENTION

The present invention relates to a tubus for defining the boundary of a beam of penetrating rays, and which incorporates means for facilitating the manipulation thereof.

In the radiation therapy it is known to interpose a tubus between the patient and the radiation source, whether the latter be an X-ray tube, an encapsulated radiation head with a radioisotope, or an electron accelerator. Hereby, the tube is placed into position on the body of the patient. This has the particular advantage that there is thus defined the distance of the radiation source from the patient and, as a result, also the applied dose rate. Moreover, the application of such tubuses presents the advantage that the unweakened radiation only impinges onto the region of the body surface which is encompassed by the edge of the tubus so as to be readily recognizable by the operating personnel. Additionally, the stray radiation emanating from the patient is absorbed by the tubus, insofar as it exits within the region of the tubus. However, it has been found to be disadvantageous for the irradiation of differently sized and differently shaped illness spreads, that this necessitates a large supply of tubes of all sizes. In actual practice this leads to that the tubus which is fastened to the radiation source, and which is quite heavy due to its radiation shielding, must be exchanged after each radiation treatment, and must be replaced by a tubus which is suited to the subsequent patient. In addition thereto, frequently there must be experimented with one and the same patient as to which tubus can best be utilized. The foregoing all leads to a multiplicity of exchanges of the tubuses before the beginning of each radiation treatment. Even with a large selection of such tubuses, whose storage is connected with a considerable financial expenditure, there will always occur instances in which the one tubus is too small and the other tubus too large, or in which the external configuration of the tubus is not optimally correlated with the region which is to be irradiated, so that also healthy tissues can be damaged.

SUMMARY OF THE INVENTION

Accordingly, it is an object of the present invention to provide a tubus for defining the boundary of a beam of penetrating rays, which is preferably adapted for use in the radiation therapy. This tubus should provide the possibility of reducing the extent of labor which increases for the operating personnel through the frequent exchanging of the tubuses, and also the requirements for the storage of the tubuses.

Inventively, in a tubus of the above-mentioned type, the tube wall is thereby constructed of a plurality of overlapping wall elements directed in parallel with the edge radiation of the radiation cone encompassed by the tubus, and suspended on the tubus housing so as to be displaceable perpendicular to the direction of the edge radiation. That type of construction of the tubus facilitates the cross-section and also the surface of the focused radiation cone to be varied. Thereby it becomes possible to correlate the radiation field in a stepless manner by means of one and the same tubus over a widge range to almost every form and size of the illness spread. This again leads to that the exchanging of the tubes may be restricted to infrequent specialized surfaces.

Although it is known to adjust a radiation area to an almost desired size by means of diaphragm plates arranged in perpendicular to the radiation direction and displaceably supported within their plane, in this instance, all of the disadvantages inherent to a free, not fully encompassed radiation cone must be assumed. These disadvantages, amongst others, are a not absolutely determined spacing and, thereby, a not determined dose rate, an increased subjecting of the environment to stray radiation, as well as a not immediately recognizable expansion of the radiation area or field.

A particularly practical construction of the tubus is attained when, in a particularly advantageous modification of the invention, the wall elements of each tubus side are guided on a shaft which is directed in parallel to this tubus side and perpendicular to the symmetrical axis of the tubus, and which is displaceably supported on the tubus housing. Through this type of guiding of the wall elements there becomes possible a construction in which the patient-sided ends of the wall elements may be maintained free of mounting or support locations. The support of the wall elements may, in actuality, be provided in the middle region of the wall elements and on the outside thereof. Consequently, the expansion of the tubus on the side facing towards the patient, similar as with a rigid or fixed tubus, is determined only by means of the measurement of the wall of the tube encompassing the radiation cone in conformance with the currently set diameter. This affords a good accessibility to the radiation areas or field.

In an entirely particularly advantageous construction of the invention, the middle wall element of each tubus side may be provided with an angled lever for pivoting in conformance with a suspension in the virtual focal point of the radiation source, whose free end extending from the plane of the wall element is guided in a groove which is introduced in a guide portion fastened to the tubus housing so as to extend approximately perpendicular to the plane of the wall element. Hereby the support location about which the wall elements are pivoted upon adjustment of the tubus width and which, due to the orientation of the wall elements in parallel to the edge radiation of the currently focused radiation cone, must be located in or at least in direct proximity to the focal point of the radiation, may be arranged remotely located from the focal point of the radiation. This is of unestimable advantage at all radiation sources since, in actual practice, a support of the diaphragm plates in direct proximity of a radiation source is practically impossible. Due to this guidance of the diaphragm plates at a location which is remotely positioned from the focal point of the radiation, it is possible in connection with the displaceably supported shaft, that the diaphragm plates may be supported exteriorly of the radiation cone which is to be presently focused at a suitable location, and to still pivot them about an imaginary rotational point which is located in the focal point of the radiation.

The guidance of the diaphragm plates may be constructed so as to be still more precise when the two ends of each shaft are each provided with a pinion for the parallel guidance of the shaft, which run in gear racks along the sides of the tubus housing and which are fastened in parallel to these sides. In this manner there is excluded a tilting or canting of the shafts and the diaphragm plates.

BRIEF DESCRIPTION OF THE DRAWINGS

Further details and advantages of the invention may now be ascertained from an exemplary embodiment thereof, taken in conjunction with the accompanying drawings; in which.

DETAILED DESCRIPTION

Figure 1:
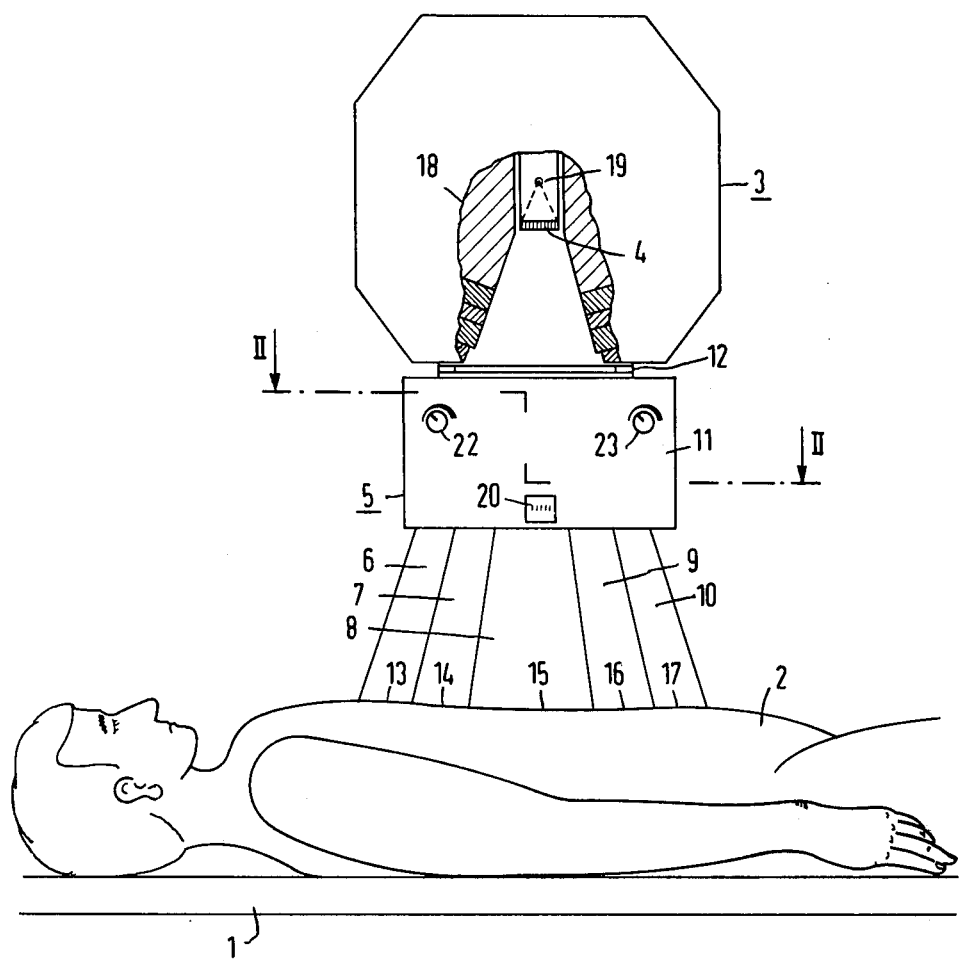
FIG. 1 illustrates, partly in section, a radiation head with an inventive tubus connected thereto, and a patient who is to be irradiated.

In FIG. 1 there may be ascertained a patient 2 lying on the patient support palette 1, a radiation head 3 with a radiation source 4, and a principal tubus 5 for defining the boundary of the radiation cone. FIG. 1 clearly illustrates that the wall structure of the tubus is constituted of individual mutually overlapping wall elements 6, 7, 8, 9, 10. A tubus housing 11 is fastened on the radiation head 3 by means of a flange 12. The radiation head 3 is lowered down so far towards the patient, whereby the wall elements of the tubus, with the edges 13, 14, 15, 16, 17 facing the patient, will lie on the patient 2. Through a section 18 shown in the wall of the radiation head 3 there may be recognized the arrangement of the wall elements of the tubus 5 relative to the virtual focal point 19 of the radiation source 4, in the exemplary embodiment of FIG. 1 consisting of a radioisotope. Recognizable on the tubus housing 11 is one of two indicators 20, 21 (FIG. 3), from which the aperture width of the tubus can be read off, as well as two adjusting knobs 22, 23, for effecting the presetting of the tubus aperture.

Figure 2:
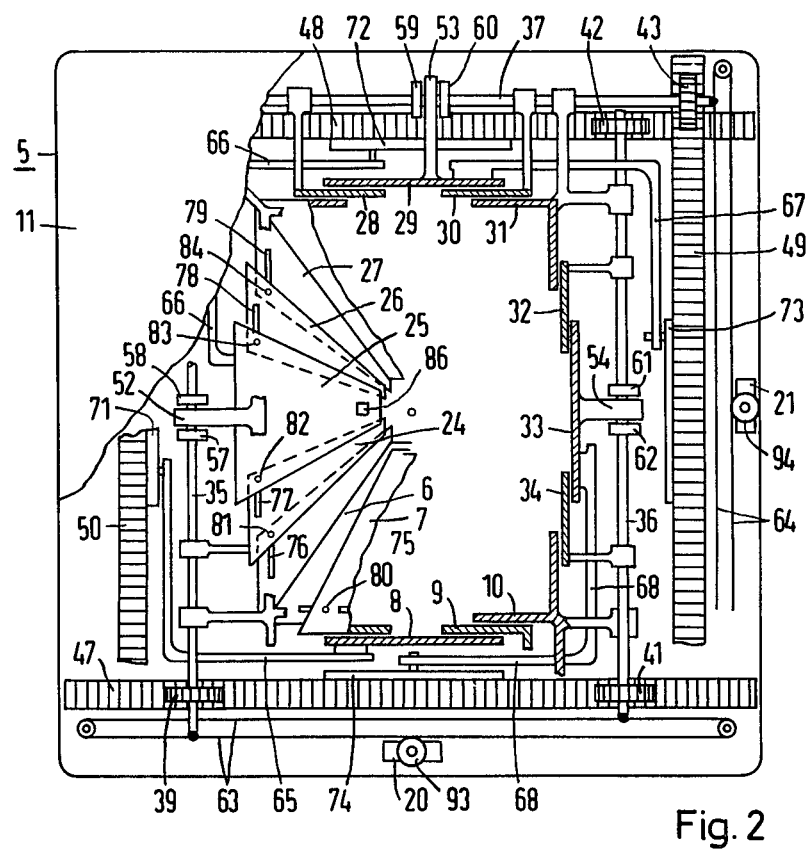
FIG. 2 is a sectional view through the tubus taken along line II—II in FIG. 1.
Figure 3:
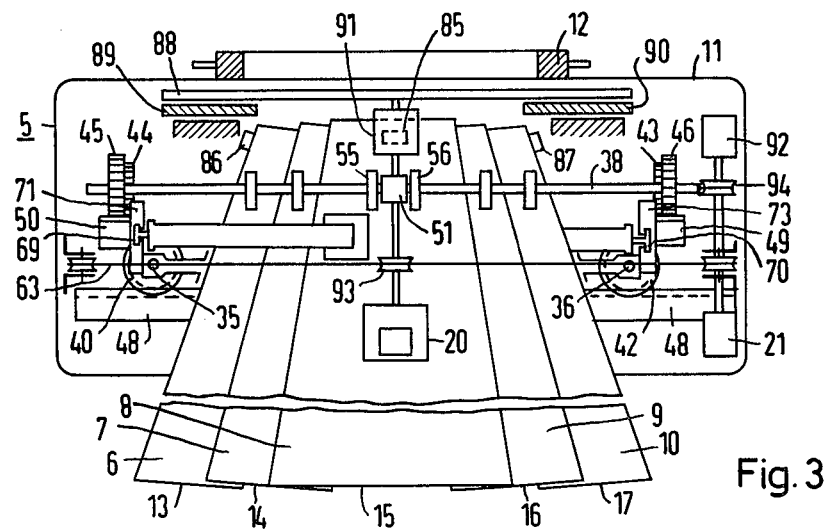
FIG. 3 is a side view of the tubus, with the tubus housing shown in section.

FIG. 2 illustrates a section taken along line II—II in FIG. 1 in a direction viewed from the radiation source. Through the tubus housing 11, shown extensively broken open, there may be recognized the support and guidance of the diaphragm plates 6, 7, 8, 9, 10, 24, 25, 26, 27, 28, 29, 30, 31, 32, 33, 34 within the tubus. Finally FIG. 3 shows the same tubus 5 from the side wherein the forward portion of the tubus housing 11 has been eliminated in the viewing direction for purposes of clarity. Particularly in FIG. 2 there may be readily recognized the construction of the tube wall structure of 16 roof shingle-like overlapping wall elements 6 through 10 and 24 through 34. With the exception of four wall elements 6, 10, 27 and 31 which have an angled cross-section and which define the corners of the focused and essentially rectangular radiation area, the remaining wall elements are planar, trapezoidally shaped plates. Supported within the tubus housing 11 in parallel with each of the four sides of the radiation field which is to be focused is respectively a shaft 35, 36, 37, 38, which carries at both ends thereof, respectively, a small gear or pinion 39, 40, 41, 42, 43, 44, 45, 46, which rolls on a gear rack 47, 48, 49, 50 fastened on the tubus housing 11 in parallel with the two adjacent tubus sides. Supported on each of these shafts are all of the wall elements which extend in parallel therewith. Thereby, the middle wall element 8, 25, 29, 30 of each tube side is restricted from axial displacement along the shaft by two discs 55, 56, 57, 58, 59, 60, 61, 62 on both sides of its support 51, 52, 53, 54 on the associated shaft 35, 36, 37, 38 which are pinned together with the shaft. The shafts on the oppositely located sides of the tubus run on common gear racks 47, 48 and 49, 50 which are located in the same plane, whereas the gear racks of the shafts which are offset by 90° thereto are located in another plane. The mutually parallel shafts on the opposite sides of the tubus are oppositely adjustable relative to each other by means of a motor-driven adjustable cable line 63, 64. The middle wall element 8, 25, 29, 33 of each tube side carries an angled lever 65, 66, 67, 68, the latter of which is displaceably located with its free end in a groove 69, 70 (FIG. 3) in a guide element 71, 72, 73, 74, fastened to one of the associated gear racks 47 through 50. Through inclination of these grooves, by means of the presently angled lever 65, 66, 67, 68, there is determined the inclination of the associated middle wall element 8, 25, 29, 33 about the axis of the corresponding shaft 35, 36, 37, 38 at all aperture widths of the wall elements. The presently adjacent wall elements 6, 7, 9, 10, 24, 25, 26, 27, 28, 29, 30, 31, 32 and 34 are connected among each other so as to be displaceable within their plane through grooves 75, 76, 77, 79 and headed pins 80, 81, 82, 83 and 84 running in these grooves. Thereby is achieved that the wall element will always overlap each other and be also directly closely superimposed. In FIG. 3 there may be further recognized that the middle wall elements 8, 25, 29, 33 of each of the tubus sides have on the edges facing towards the radiation source a small guide gear 85, 86, 87 into which there may be hooked cover plates 88, 89, 90 which are displaceably supported in the tubus housing 11 perpendicular to the radiation direction similar to diaphragm plates of conventional radiation shutter. The cover plates 88, 89, 90, at smaller tubus openings, prevent leakage radiation between the tubus flange 12 and the wall elements 6 through 10, 24 through 34. In the illustration of FIG. 3 there may be also ascertained that the actuating motors 91, 92 for the wall elements, in addition to the cable lines 93, 94 for the displacement of the shafts 35, 36, 37, 38 and the wall elements supported on the shafts also drive the two indicator arrangements 20, 21 for the aperture of the tubus 5.

Should a patient be irradiated, then the width of the tube is adjusted by means of setting knobs 22, 23 which may have a servocontrol associated therewith, not illustrated herein for purposes of clarity. Hereby are switched in the two actuating motors 91 and 92. These run for so long until, by means of the cable discs 93, 94 the cable lines 63, 64 and the shafts 35, 36, 37 and 38, the wall elements 6 through 10 and 24 through 34 have been moved into their selected position. During the adjusting movement of the shafts, not only are the wall elements which are supported on the shafts taken along, but also the angled levers 65, 66, 67, 69 displaced within their respective guide portions 71, 72, 73 and 74. The grooves 69 and 70 are so oriented within these guide portions so that the present middle wall elements 8, 25, 29 and 33 of each tube side will incline as to presently coincide with the imaginary or virtual focal point 19 of the radiation source. The angled wall elements 6, 10, 27 and 31 at the four corners of the tubus 5 are concurrently supported on two adjacent shafts. The linkage structure which leads to the shafts is linkably fastened to the angled wall elements. By means of the grooves 75, 79 and the guide pins 80 through 84 of the wall elements, the wall elements are supported in all angled positions in overlapping relationship and in direct contact with each other.

Figure 4:
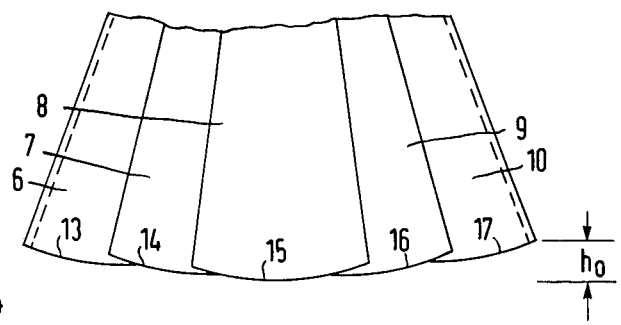
FIG. 4 is a side view of the patient-sided border edges of the wall elements of the tubus of FIG. 1.
Figure 5:
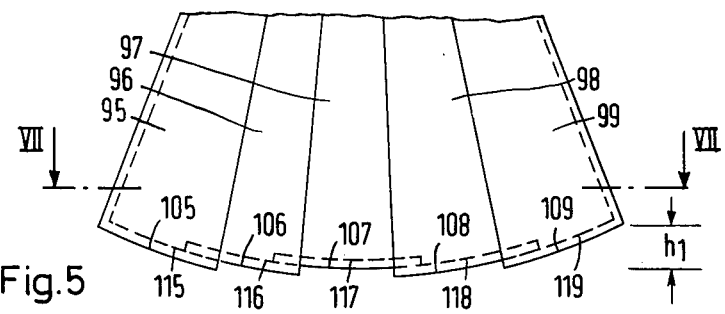
FIG. 5 is a side view of a modified embodiment of the patient-sided border edges of the wall elements.
Figure 6:
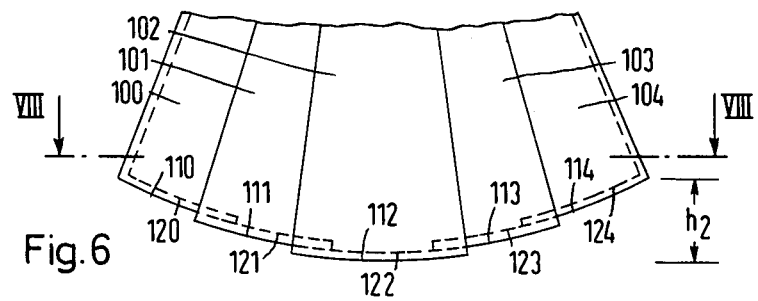
FIG. 6 is a side view of a further modified embodiment of the patient-sided border edges of the wall elements.

FIGS. 4, 5 and 6 illustrate the construction of the edges of the wall element facing towards the patient. While the wall elements 6, 7, 8 and 9 and 10 which are shown in FIG. 4 extend completely straight on the patient-sided edges 13, 14, 15, 16, and 17, the wall elements 95, 96, 97, 98, 99, 100, 101, 102, 103, 104 of the embodiments of FIGS. 5 and 6 are each provided at their patient-sided edges 105, 106, 107, 108, 109, 110, 111, 112, 113, 114 with respectively an edge beading 115 through 124 projecting interiorly of the tubus. By means of this edge beading, the radiation cone which lies in immediate proximity to the wall elements, and due to stray radiation evidences a somewhat weakened dose rate, can be absorbed. The remaining radiation field which is focused by the edge beading thus evidences a somewhat more uniform intensity dropoff. As a result of the required overlapping of the edge beadings, the wall elements must now be stepped with respect to each other along their lengths in the ray or beam direction. There are provided two possibilities for the construction of the wall elements which are illustrated in FIG. 5 and 6. Whereas, in the embodiment of FIG. 5, the wall elements 95, 99 which are provided with an angled profile are located externally on the immediately adjacent wall elements, in the embodiment of FIG. 6 this is precisely the opposite. Through the external superposition of the angled wall elements 95, 99 onto the wall elements 96, 98 which are positioned more closely towards the middle of each tube side, pursuant to FIG. 6 there is achieved an improved lengthwise stepping and thereby also a better contact of the wall elements 95 to 99 with the patient. This may be readily recognized on the small height distinction $h1$ between the corners and the middle of each side wall of the tubus in FIG. 5. In the exemplary embodiment according to FIG. 6 this height distinction $h2$ is so considerable, that the wall elements 100 to 105 at an intense X-radiation and the thereby required strength of the edge beadings can no longer be brought into position on the patient at the tubus corners.

Figure 7:
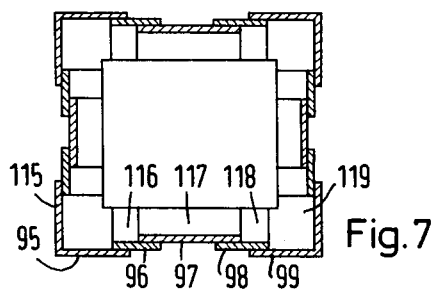
FIG. 7 is a section taken along line VII—VII in FIG. 5.
Figure 8:
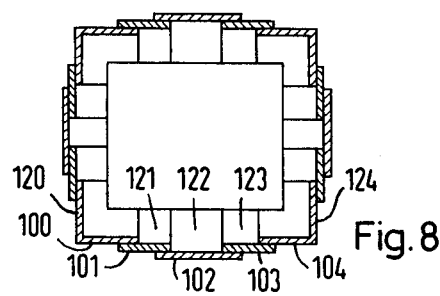
FIG. 8 is a section taken along line VIII—VIII in FIG. 6.

In FIG. 7, which illustrates a section taken along line VII—VII in FIG. 5, and in FIG. 8, which represents a section taken along line VIII—VIII in FIG. 6, there can be recognized that the edge beadings have their depths so determined with respect to each other so that there is focused a rectangular radiation field notwithstanding the roof shingle-like arrangement of the wall elements. When in the embodiment of FIG. 8 the edge beadings 104 to 108 were to be omitted, then this would correspond to a section taken through the wall elements of FIG. 4. The radiation field has a slightly spherical cross-section so that this is particularly suitable for the radiation treatment of most types or spreads of illnesses. Due to this interrelationship, for X-rays or gamma rays there must be eliminated either an embodiment of the wall elements with edge beadings, or in the corners of the radiation field positioning of the wall elements on the patient. In the first instance, in an arrangement of the wall elements according to the illustration in FIG. 4 there is produced a spherical radiation field which corresponds to the external contour of FIG. 8.

Figure 9:
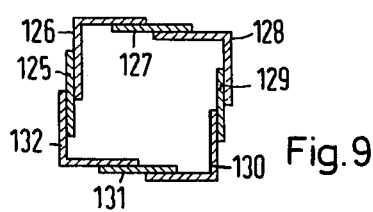
FIG. 9 shows another type of overlapping arrangement of the wall elements of a tubus.
Figure 10:
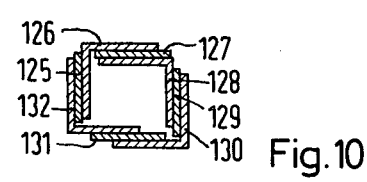
FIG. 10 illustrates the arrangement of the wall elements of FIG. 9 at the smallest possible focusing.

The relationship of maximum to minimum tubus opening becomes the larger the more wall elements are employed. FIGS. 9 and 10 illustrate an arrangement of the wall elements 125 to 132 which facilitate that, for a given relationship of maximum to minimum opening for the tubus, it will be sufficient to use only one-half as many wall elements as are used in the embodiments pursuant to FIGS. 4, 5 and 6. In this arrangement, in which the wall elements 125 to 132 lie, on one side thereof, on the adjacent wall elements and therebelow on the other side, there must be assumed an asymmetrical cross-section of the focusable rectangular radiation field. This is particularly apparent in the opened position of the wall elements, pursuant to FIG. 9.

While there has been shown what is considered to be the preferred embodiment of the invention, it will be obvious that modifications may be made which come within the scope of the disclosure of the specification.

What is claimed is:

1. In a tubus for defining the boundaries of a beam of penetrating rays including a tubus housing, a plurality of mutually overlapping wall elements forming a tubus wall structure in parallel with the direction of edge radiation of a ray cone encompassed by the tubus, means for suspending the wall elements on the tubus housing for displacement perpendicular to the direction of edge radiation, the improvement comprising shaft means having a longitudinal axis for guiding and pivoting the wall elements of each tubus side for a suspension in the virtual focal point of a radiation source, the tubus having a symmetrical axis, said shaft means being supported on the tubus housing, displaceable at right angles to said longitudinal axis and extending in parallel with the tubus side associated therewith, and perpendicular to the symmetrical axis of the tubus; lever means for controlling the inclination of the wall elements with respect to the tubus symmetrical axis; and guide means for guiding said lever means.

2. A tubus as claimed in claim 1, wherein said shaft means includes a plurality of shafts and comprising a pinion being fastened to each end of each of said shafts for parallel guidance of said shafts, respectively; and gear rack means being fastened to the sides of said tubus housing in parallel with said sides, said pinions being in cooperative engagement with said gear rack means.

3. A tubus as claimed in claim 1, each of said wall elements having one side thereof positioned exteriorly and the opposite side interiorly of a presently adjoining wall element.

4. A tubus as claimed in claim 1, each of said wall elements having an inwardly projecting ray-absorbing edge beadings at the patient-sided end thereof, said edge beading being mutually stepped for overlapping thereof in their respective spacings from the source of the radiation.

5. A tubus as claimed in claim 1, said tubus wall structure comprising angle-profiled wall elements at each of the four corners thereof for an approximately rectangular cross-section of a focusable radiation area, and at least one planar wall element located intermediate two of said angle-profiled wall elements.

6. A tubus as claimed in claim 5, comprising an angled lever being fastened to a middle wall element of each said tubus side for pivoting pursuant to said guide means being fastened to said tubus housing, a groove in said guide means extending generally perpendicular to the plane of said middle wall element, said angled lever having a free end projecting out of the plane of said wall element being guided within said groove.

7. A tubus as claimed in claim 5, comprising an odd number of planar wall elements being located intermediate two of said angle-profiled wall elements, the middle one of said planar wall elements being located externally of the side edges of the wall elements located more proximate the side edges of said tubus.

* * * * *